United States Patent [19]

Takahashi et al.

[11] 4,058,737
[45] Nov. 15, 1977

[54] METHOD AND APPARATUS FOR DETECTING EXTRANEOUS SOLID SUBSTANCES CONTAINED IN LIQUID

[75] Inventors: Toshio Takahashi, Honjo; Toshiyasu Ehara, Misato; Ryosaku Tagaya; Mikio Tagaya, both of Isezaki, all of Japan

[73] Assignee: Eisai Co., Ltd., Tokyo, Japan

[21] Appl. No.: 669,958

[22] Filed: Mar. 23, 1976

[30] Foreign Application Priority Data

Mar. 25, 1975  Japan .................................. 50-34898

[51] Int. Cl.² .............................................. G01N 21/26
[52] U.S. Cl. .................................... 250/573; 250/227; 356/103
[58] Field of Search .............. 250/573, 574, 576, 227; 178/7.6; 350/96 R, 96 B; 356/103, 104

[56] References Cited

U.S. PATENT DOCUMENTS

| | | | |
|---|---|---|---|
| 3,238,294 | 3/1966 | Krauss | 178/7.6 |
| 3,325,594 | 6/1967 | Goldhammer et al. | 250/227 |
| 3,627,423 | 12/1971 | Knapp et al. | 250/573 |
| 3,800,149 | 3/1974 | Lang | 250/227 |

*Primary Examiner*—David C. Nelms
*Attorney, Agent, or Firm*—Wenderoth, Lind & Ponack

[57] ABSTRACT

An improvement of a method and an apparatus for detection of an extraneous solid substance which may exist in a transparent liquid wherein a sealed transparent container filled with the transparent liquid is rotated to cause rotation of the extraneous solid substance mixed and floated in the liquid. Light is projected through the container and the intensity of the light passed through said container is measured. The invention is characterized in that an optical fiber line-circle converter has its linear end formed into two or more straight files which may be set on the same or different level lines, respectively. The present method and apparatus can detect more precisely the extraneous substance moving in an irregular motion in the transparent liquid.

9 Claims, 3 Drawing Figures

METHOD AND APPARATUS FOR DETECTING EXTRANEOUS SOLID SUBSTANCES CONTAINED IN LIQUID

The present invention relates to a method for inspecting an extraneous solid substance which may exist in a transparent liquid filled in a sealed transparent container.

BACKGROUND OF THE INVENTION

For inspecting solids which may exist in a liquid such as medicine, food and drink, cosmetic, chemicals, reagent or the like, filled in sealed, transparent containers, for example, ampoules, vials, bottles or the like, and to select the containers, there are known various methods for inspection the liquid utilizing the photoelectric element rather than relying simply on the a naked eye inspection.

Among these known methods for inspecting a liquid, the present invention attempts to improve the liquid testing method for determining the intensity of a penetrated light wherein light is projected, for example, through an ampoule) by measuring the degree of the screening of said light due to extraneous substances existing within a liquid by a photoelectric element. In such a case the light is screened by extraneous substances and the light received by the photoelectric element is decreased relative to the amount that is present when an extraneous substance is absent. Therefore, whether the amount of extraneous substances in a liquid is large or small, can be determined according to the decrease of light received by the photoelectric element.

SUMMARY OF THE INVENTION

An object of this invention is to provide a means whereby it is possible to precisely detect the extraneous substances being moved in a peculiar motion in the liquid. Namely, the present invention relates to a method for detecting the existence of solids in a transparent liquid by rotating a sealed, transparent container filled with a transparent liquid, to rotate solids which may exist in the liquid, projecting light in to the container, and measuring the intensity of the light which is passed through said container and not intercepted due to the substances. The method is characterized in that a linear end of an optical fiber line-circle converter is formed into two or more straight files.

Another object of this invention is to provide an optical fiber line-circle converter which is constructed to avoid the dispersion of brightness caused by the varied position of the substance to be detected in the container, and which has in particular, linear ends formed into an even number of straight files.

A further object of this invention is to provide an optical fiber line-circle converter capable of detecting more precisely an extraneous solid substance moving in peculiar motions, which comprises forming a linear end of said converter into two or more files set on different level lines respectively, so that the image of the extraneous substance can be received at different distances from the image lens.

BRIEF DESCRIPTION OF THE DRAWINGS

The present invention will be described with reference to an embodiment shown in the accompanying drawings.

DETAILED DESCRIPTION OF THE INVENTION

Figure 1:
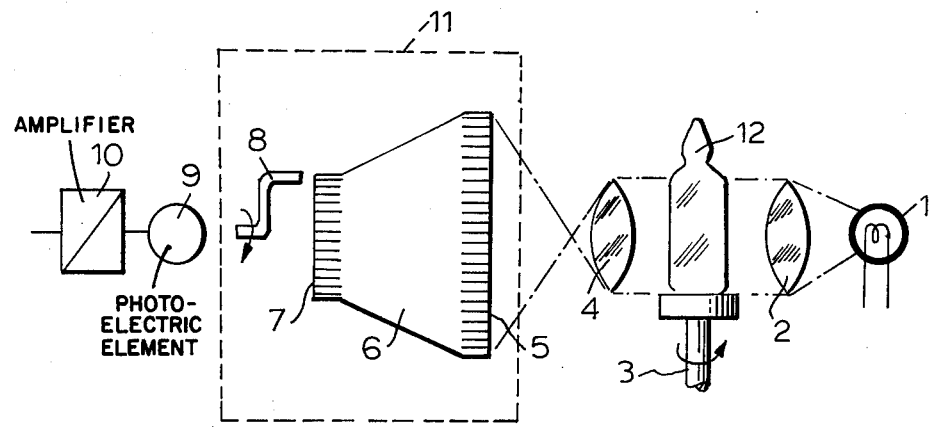
FIG. 1 is an arrangement diagram of an apparatus showing one embodiment of the present invention.

In the arrangement diagram shown in FIG. 1, a lamp or light projecter 1 is lighted to provide parallel rays of light from a condenser lens 2 placed in front thereof, and the parallel rays of light are projected against an ampoule 12 to be inspected which is 3. The turntable 3 is rotated at a high speed and then stopped suddenly, so that extraneous substances existing in the ampoule fixed on the turntable are rotated together with the liquid in the ampoule. Projected images of the extraneous substances are then made on the straight ends 5 and 5' of optical fiber 6 of a scanner 11 by an image lens 4, which interrupt the direct rays of light from the lamp 1 thrown onto the light-receiving faces of the optical fibers. Thus, darkened areas caused by the screening of the projected light is transmitted to the circular end 7 through the optical fibers 6. The condition of the circular end 7 is minutely picked up by a rotating scan head 8, and transmitted to the light-receiving face of a photoelectric element 9 where it is there converted into electrical pulse signals. The amplified signals are produced in an amplifier 10. Thus, the presence of an extraneous solid substance in the ampoule is detected and converted to electrical pulse signals. By utilizing these signals the selection of the ampoule on the basis of solid impurities can be carried out.

In the scanner, a plurality of minute light-receiving faces are arranged in a straight lines. These light-receiving faces each have an area at least corresponding to the size of the image of the extraneous substance predetermined as the minimum limit to be caught by a bundle of the optical fibers of the optical fiber line-circle converter. The faces are arranged in a straight file, which is so made up that scanning is carried out in turn on these minute light-receiving faces one by one.

Figure 2:
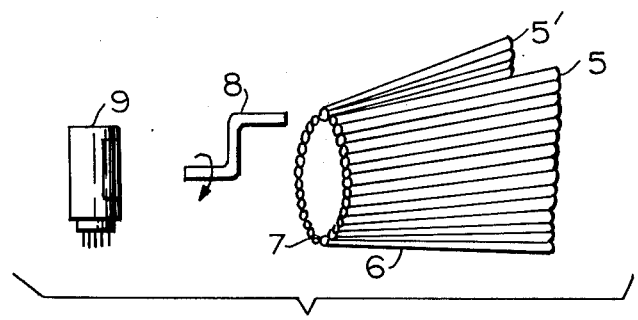
FIG. 2 is an enlarged, oblique view of the optical fiber system scanner of one part shown in FIG. 1.

The optical fiber system scanner will be described with reference to the enlarged, oblique view in FIG. 2. FIG. 2 shows an embodiment of the scanner 11 equiped with an optical fiber line-circle converter utilizable in the scanner, in which converter the light-receiving portions thereof are arranged for two straight files. This optical fiber system scanner has a number of optical fibers 6, for example as slender as 100μ in diameter, a rotary scanning head 8 and a photoelectric element 9. These plural optical fibers are at one end thereof arranged into two straight files, i.e. linear end 5 and 5', and at the other end the fibers are arranged circularly so as to form a circular end 7 (a line-circle conversion structure). One end of the rotary scanning head 8, which is made of optical fiber, rotates and scans along said circular end 7 and the other end of this scanning head 8 is optically connected to the light-receiving face of the photoelectric element 9. Through an ampoule, which has come to a sudden stop from a high speed rotation, the light from the light source is thrown to the light-receiving faces of minute cross section in the linear ends 5 and 5', and gives a constant brightness to the light-receiving faces. When the projected image of any extraneous substance existing in the ampoule crosses the linear ends 5 and 5', the light-receiving faces of the optical fibers are darkened, because the direct rays of light from the source are screened by the extraneous substances. Such a bright or dark state at the linear ends 5 and 5' is transmitted to the circular end 7 through the optical fibers 6, and the rotating scanning head 8 picks up the brightness and darkness of each one of the optical fibers at the circular end 7 while it is rotated. These conditions are then converted to the intensity of an electric current by the photoelectric element. Based on these electrical signals, the inspection and selection of the object may be carried out properly in a known manner.

According to the above-mentioned embodiment of the present invention, the screening of the light on the light-receiving faces of the optical fibers due to the extraneous substances is utilized for measurement and, therefore, signals having a higher S/N ratio can be obtained even when an extraneous substance having a small refractive power exists, whereby a highly accurate determination can be achieved. Since the size of the projected image which is the same as the diameter of each one of the optical fibers is the size of the minimum extraneous substance which can be detected, the minimum size of a catchable extraneous substance can be freely changed by adjusting the magnification of the image lens.

Figure 3:
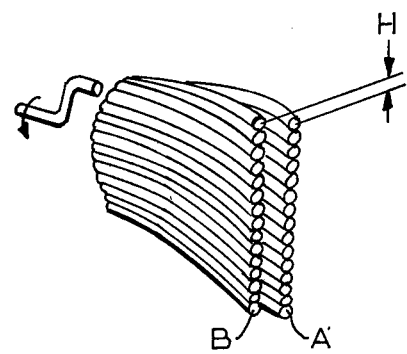
FIG. 3 shows another embodiment in which the linear end of the optical fiber converter is formed into two files A and B set on different level lines.

In FIG. 3, the files A and B may be directly adjacent to each other or interruped by, for example, a fixed means etc.

When it is desired to detect a minute extraneous substance having for example a minimum size of 10μ, an optical fiber having corresponding diameter, 10μ, should be employed. However, the smaller the optical fiber is, the more difficult it is to manufacture the scanning device. Then, the detection is achieved generally by optically enlarging the image of the minute extraneous substance. In such a case, there can not be avoided lowering of focal depth due to the optical enlargement, and so, it is difficult to detect the minute extraneous substance moving to change the position thereof.

In the present invention, since there is provided a level difference H, which may be selectively determined between the light-receiving faces of the linear end A and that of B, it is possible to receive an image of the extraneous substance at two positions different in the distances from the image lens, respectively. Even when the focal depth is lowered by optical enlarging, it is easier to focus on the image, because it is possible to focus at two or more points.

Also, when the extraneous substance is moved by a distance equal to the radius of the container to be inspected, an optical image of the extraneous substance can be clearly focussed either the end A or the end B; that is, the focusing area of the extraneous substance can be extended. Thus, the present method exhibits an excellent effect for the precise detection of the extraneous substance moving in an irregular motion.

According to the foregoing statements, the present invention is characterized in that the light-receiving portions of an optical fiber in an optical fiber line-circle converter are at one end arranged in two or more straight files of linear displacement so that a large number of the optical fibers 6 may be used and, therefore, the number of chances for catching the light received on the optical fibers in every single revolution of a rotating scan head is increased. It may be expected in this invention that substantially the same effect is obtained as that achieved when the revolutions of the rotary scanning member are increased as compared with a conventional scanner in which the ends of optical fibers are formed into an single linear end. Additionally, in this invention two or more plural lines having linear ends are formed so that the number of light-receiving positions for the object is increased, thus providing many chances of catching the images of extraneous substances in accordance with the increased number of said positions. Moreover, the measurement does not undergo any influence of the dispersion in brightness effected by the position of the object. For example, when there is the dispersion in brightness between the upper portion and lower portion of the object, in a conventional scanner having a single linear end, the difference of brightness between the upper and lower portions of the object is immediately shown in electrical signals, which is apt to be mistaken for the signals based upon the extraneous substances, because the optical fiber of the lowermost end and the optical fiber of the uppermost end at the linear end 5 and 5', are adjacent to each other on the circle end 7. On the other hands, the present invention does not undergo the influence of the dispersion in brightness, because the optical fiber line-circle converter has one end thereof into two or more files, then, for example, in cases of the two lines of linear ends, the optical fiber line-circle converter can be made into a structure such that an optical fiber of the uppermost end in the first line of the linear end and the one of uppermost end in the second line, and then the lowermost end in the second column and the lowermost end in the first column are respectively adjacent to each other at the circular end.

As described above, the desirable effects are obtained by forming the linear end of the optical fiber line-circle converted into even number of files.

What is claimed is:

1. A method for determining the presence of an extraneous solid substance which may exist in a transparent liquid contained in a clear container, said method comprising:
    rotating said container on a rotary turntable, whereby the contents of said container are rotated;
    stopping rotation of said container;
    projecting light from a light source adjacent said container through said stopped container and liquid therein;
    receiving said light projecing through said stopped container which is not blocked by solid substances in said liquid in the light receiving end of an optical fiber line-circle converter having a plurality of parallel straight, linear files at the light receiving end thereof and formed into a single circle at the light emitting end, and allowing said light to transmit through said optical fibers of said converter to the circle end thereof;
    detecting the light transmitted to the circle end of said converter with a rotating scan head spaced from and rotating about said circle end; and
    optically connecting said scan head to a photoelectric member.

2. A method as claimed in claim 1 wherein said plurality of files of optical fibers at the line end of said converter are an even number of files.

3. A method as claimed in claim 1 wherein said plurality of files of optical fibers at the line end of said converter are spaced different distances from said container.

4. A method as claimed in claim 1 wherein said plurality of files of optical fibers at the line end of said converter are all an equal distance from said container.

5. An apparatus for determining the presence of an extraneous solid substance which may exist in a transparent liquid contained in a clear container, said apparatus comprising:
   a light source;
   rotatable turntable means adjacent said light source for supporting and rotating said container thereon;
   first lens means between said light source and said container on said turntable for collimating the light rays from said light source toward said container;
   a photoelectric member;
   scanning means between said photoelectric member and said container for receiving the light rays passing through said container which are not blocked by said solid substances in said liquid, said scanning means being optically connected to said photoelectric member and comprised of:
   an optical fiber line-circle converter having a linear end of a plurality of parallel, straight linear files of optical fiber directed toward said container and a circular end formed into a single circle from said fibers at the end of said fibers opposite said linear end, and
   a rotating scan head means at the circular end of said converter for scanning said fibers, said scan head means being optically connected to said photoelectric member;
   an amplifier connected to said photoelectric member; and
   a focusing lens means between said container and the linear end of said converter for focusing the light rays passing through said container onto said linear end of said optical fiber converter.

6. An apparatus as claimed in claim 5 wherein said plurality of files of optical fibers at the line end of said converter are an even number of files.

7. An apparatus as claimed in claim 5 wherein said plurality of files of optical fibers at the line end of said converter are spaced different distances from said container.

8. An apparatus as claimed in claim 5 wherein said plurality of files of optical fibers at the line end of said converter are an equal distance from said container.

9. An apparatus as claimed in claim 5 wherein the top fibers in said plurality of files at the linear end of said converter are adjacent to each other in the circular end of said converter and the bottom fibers in said files at the linear end are adjacent to each other in the circular end.

* * * * *